United States Patent [19]
Fujitsu et al.

[11] Patent Number: 5,464,405
[45] Date of Patent: Nov. 7, 1995

[54] BIPOLAR SURGICAL TWEEZERS

[75] Inventors: Kazuhiko Fujitsu, Yokosuka; Tomohiko Asahara, Tokyo; Nobuhiro Kagaminuma, Koriyama; Kohichi Iwai, Nagoya, all of Japan

[73] Assignee: Ethicon Endo-Surgery, Inc., Cincinnati, Ohio

[21] Appl. No.: 182,610

[22] Filed: Jan. 18, 1994

[30] Foreign Application Priority Data

Jan. 20, 1993 [JP] Japan .................................. 5-023481

[51] Int. Cl.⁶ ............................................. A61B 17/39
[52] U.S. Cl. ............................................ 606/51; 606/211

[58] Field of Search ................... 606/51, 52, 210, 606/211

[56] References Cited

U.S. PATENT DOCUMENTS 4,567,890  2/1986  Ohta et al. ............................... 606/51

Primary Examiner—Lee S. Cohen
Attorney, Agent, or Firm—Paul A. Coletti

[57] ABSTRACT

Embedding a perfusion passage pipe in the surface at the inside of one of the arms of a tweezers partially or entirely and concurrently, fastening a housing portion in the rear of the grip portion in a range of 90° to 170° angled from the tip portion to the central axis of the grip portion of an arm.

1 Claim, 6 Drawing Sheets

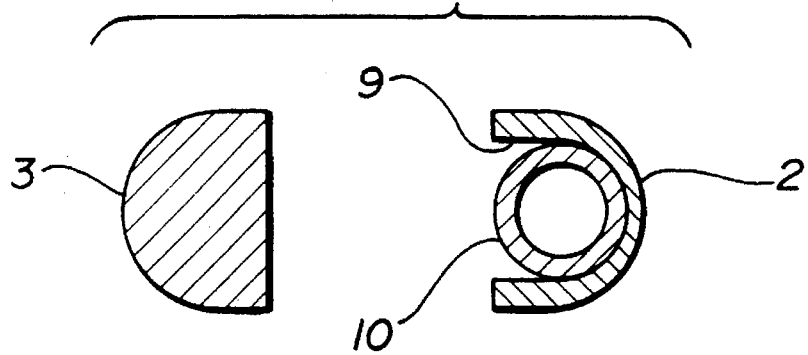
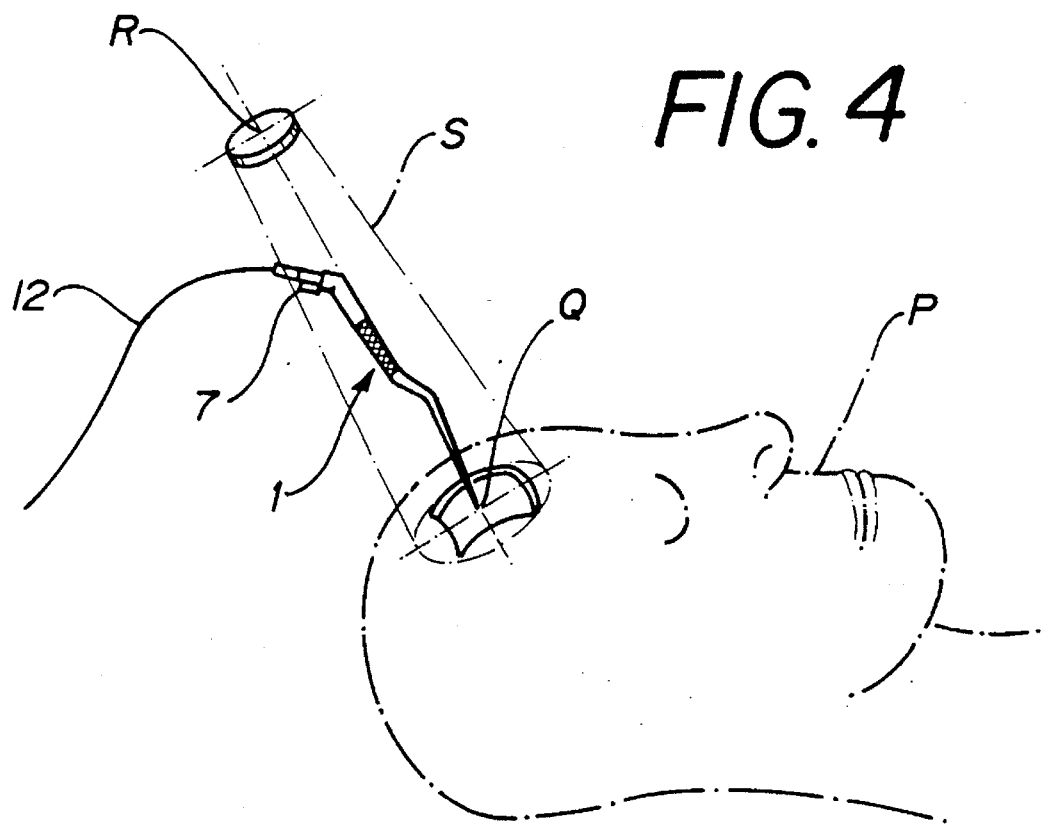

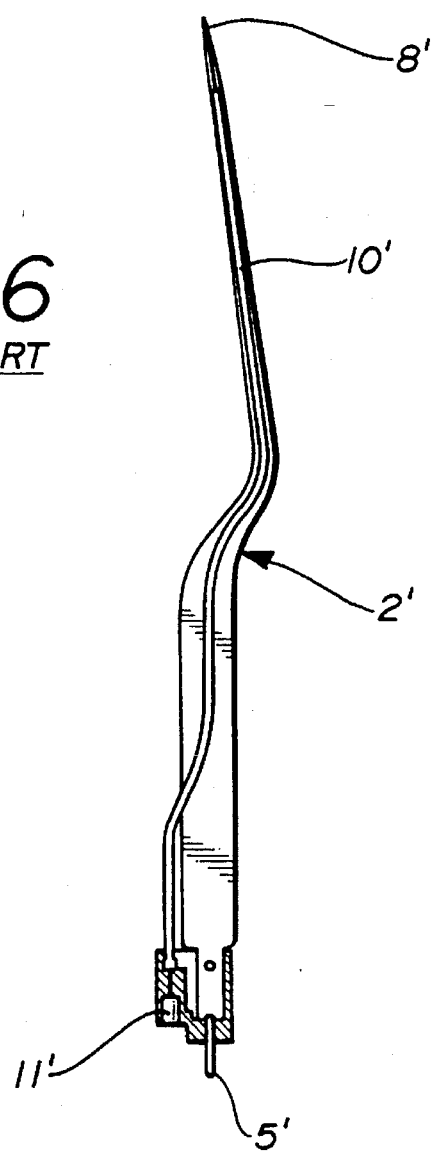
FIG. 6 *PRIOR ART*
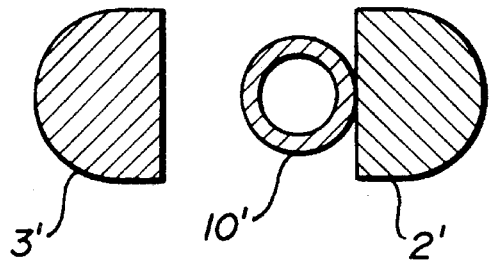
FIG. 7 *PRIOR ART*

5,464,405

BIPOLAR SURGICAL TWEEZERS

PRIORITY APPLICATION

This application claims priority from Japanese Serial No. 23481/93, filed Jan. 20, 1993.

BACKGROUND OF THE INVENTION

Bipolar electric coagulating and incising tweezers having two arms have been used in neurosurgical operations. The arms of these instruments comprise a perfusion connection port and bipolar electrodes connected to a high frequency generator, being mutually insulated and being forced so that its tip portion will maintain an open state. It has been possible to coagulate-or incise a tissue or a blood vessel by nipping such tissue or blood vessel with the tip portion of the tweezers and electrifying this with a high-frequency current. Further, there is provided a perfusion passage pipe on the surface at the inside of an arm, and a physiologic saline or any other liquid is drawn out. As a consequence, the pyrogenic temperature at the time of coagulating and incising maneuvers is lowered depending on the electrification of a high-frequency current. This makes it possible to minimize any damage to tissue and concurrently, enables one to prevent such degradation in the coagulating and incising abilities as is involved when burnt tissue portions adhere to the tip portion of the tweezers.

Shown in FIGS. 5, 6 and 7 is one example of such conventional tweezers. Since the visual field of the operator is acquired mainly by the space between the arms of bipolar electric coagulating and incising tweezers, an arrangement of a perfusion passage pipe 10' (FIG. 5) on the surface at the inside of the above arm 2' becomes an obstacle to the operator's visual field., Thus, if the nipping operation of tweezers is conducted, the tip portion 8' becomes difficult to see, in consequence of which it is hard to grasp the hemostatic or incising position exactly. Further, the arrangement of FIG. 5 also poses an obstacle to the operator's visual field, i.e., the housing portion 7' for fixing the perfusion connection port 11' and bipolar electrodes 5' 6' connected to a high-frequency generator is arranged on the straight line relative to the central axis of the arm grip portion 4'. If tweezers 1' are arranged within the operator's visual field S on the straight line ranging from the center R of the operator's visual field to the operational site as shown in FIG. 8, the above housing portion 7' and bipolar electric wire 12' come to enter into the visual field.

SUMMARY OF THE INVENTION

According to the present invention, it is an object to provide bipolar electric coagulating and incising tweezers which enable an operator to acquire his or her visual field satisfactorily in the operation, mainly in the neurosurgical operation done by using microscopes.

In order to settle the above problem, the present bipolar electric coagulating and incising tweezers are designed such that a perfusion passage pipe is embedded in the surface at the inside of one of the arms partially or entirely and concurrently, a housing portion in the rear of the grip portion fastened in a range of 90° to 170° angled from the tip portion to the central axis of the grip portion of the upper arm.

According to the present invention, it becomes possible to acquire a satisfactory visual field even during the nipping operation of tweezers by embedding a perfusion passage pipe in the surface at the inside of one of the arms of bipolar electric coagulating and incising tweezers, partially or entirely. Further, obstacles such as housing portion, bipolar electric wire or the like can be removed from the center of the operator's visual field by fastening the above housing portion in a range of 90° to 170° angled from the tip portion to the central axis of the grip portion of the above arm. This results in being able to acquire a good operator's visual field.

If the above angle is 90° or less, the housing portion becomes an obstacle at the time of griping tweezers. And if the above angle is 170° or more, this works to hinder the operator's visual field.

DESCRIPTION OF THE DRAWINGS

FIG. 3 shows a partial sectional view of tweezers pertaining to one working example of the present invention.

FIG. 4 shows a schematic layout available at the time of using the tweezers of FIG. 1 in the operation.

FIG. 6 shows a view showing the surface at the inside of one of the arms of the conventional tweezers.

FIG. 7 shown a partial sectional view of the conventional tweezers.

DETAILED DESCRIPTION OF THE INVENTION

In the following paragraphs the working examples of the present invention will be explained on the basis of the drawings.

Figure 1:
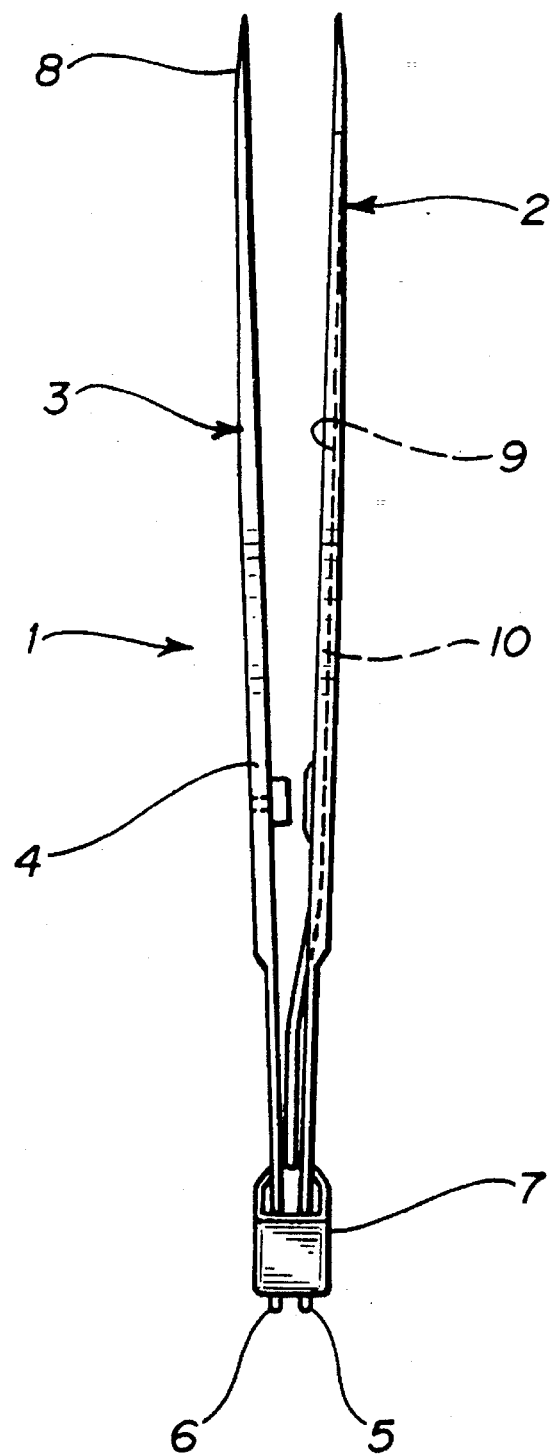
FIG. 1 shows a plan view of tweezers pertaining to one working example of the present invention.
Figure 2:
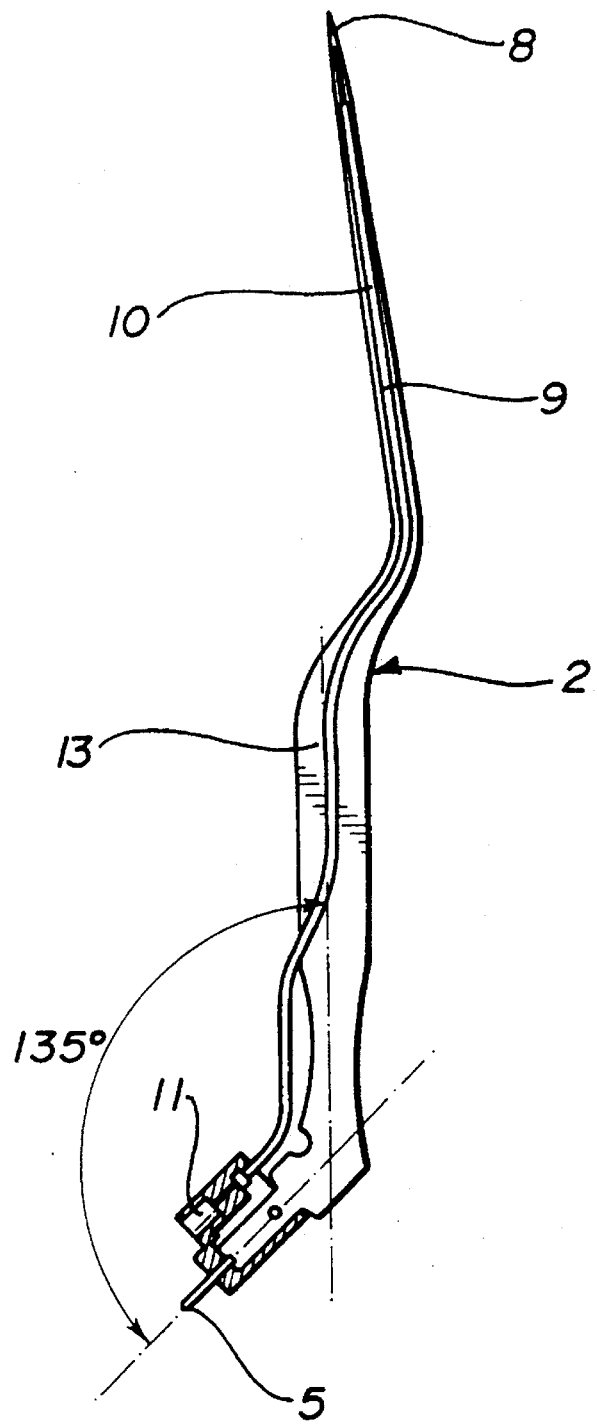
FIG. 2 shows a view showing the surface at the inside of one of the arms of tweezers pertaining to one working example of the present invention.
Figure 5:
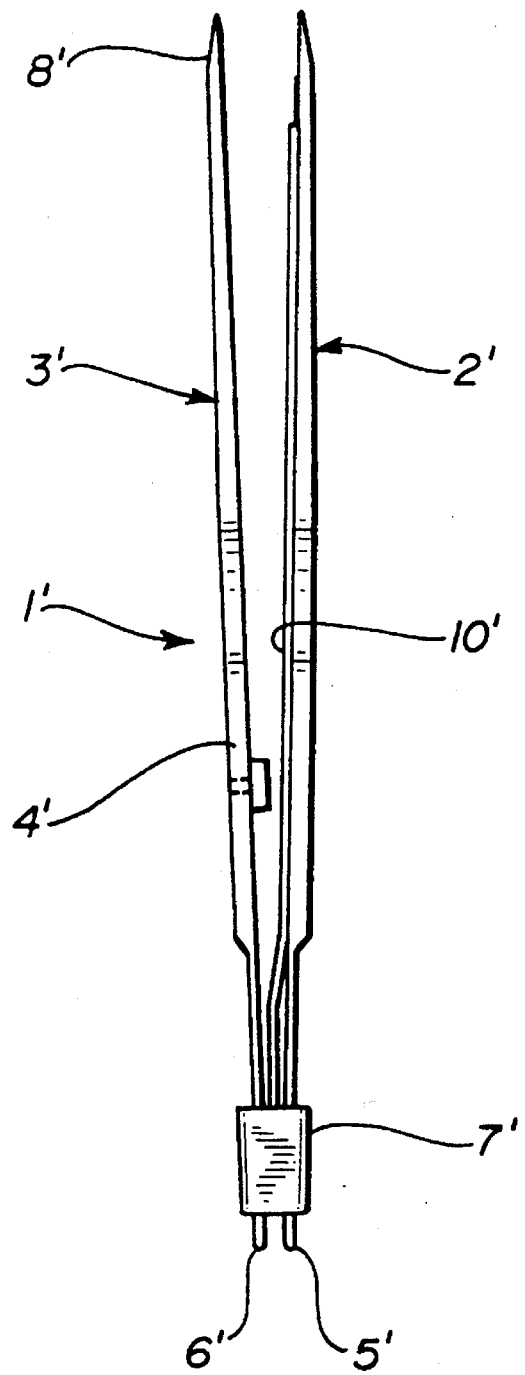
FIG. 5 shows a plan view of the conventional tweezers.
Figure 8:
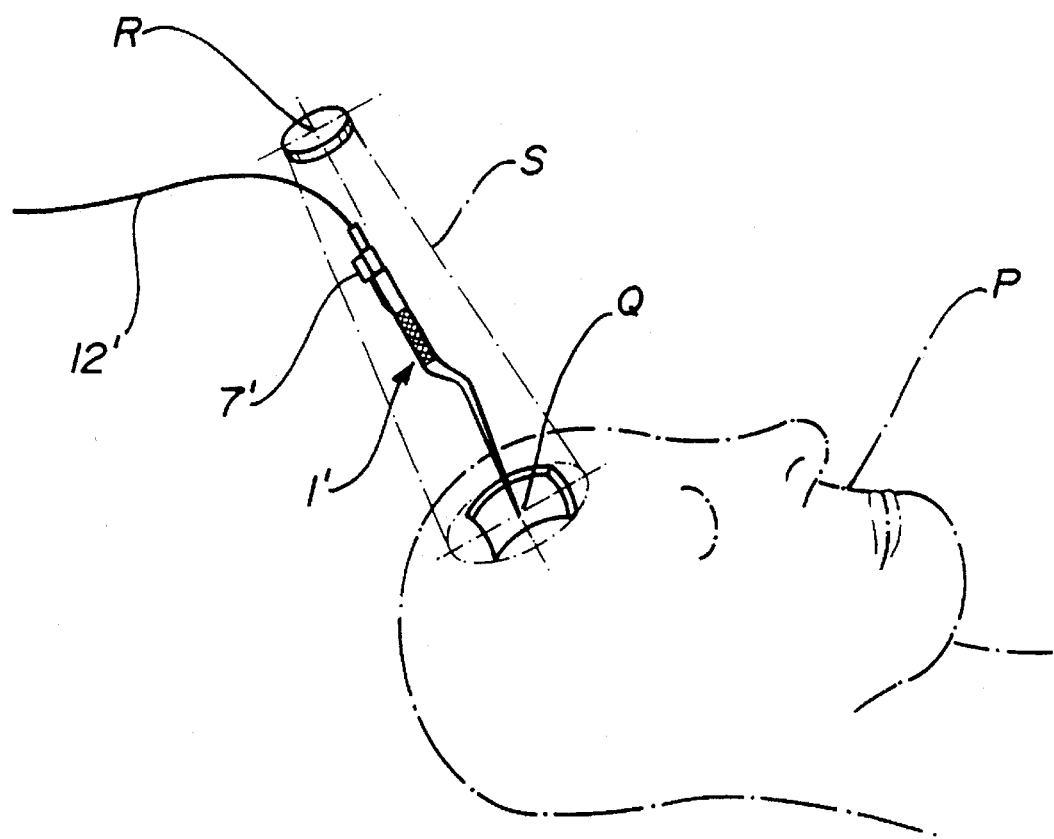
FIG. 8 shows a schematic layout available at the time of using the conventional tweezers in the operation.

FIG. 1 is a plan view of bipolar electric coagulating and incising tweezers pertaining to one working example of the present invention. FIG. 2 is a side view of the above tweezers. In the drawings, 2, 3 denote two arms each having a tip portion 8 and a grip portion 4. Each rear end side is bent by 135° from the tip 8 relative to the central axis of each grip portion 4. Further, respective arms 2, 3 are connected to respective electrodes 5, 6 and are mutually in the housing portion 7 and are fastened by being forced such that its tip portion will maintain an opening state at the normal time.

A groove 9 is made on the surface at the inside of the above arm 2 by ranging from the vicinity of the tip portion 8 to the rear of the grip portion 4 and one piece of perfusion passage pipe 10 is entirely embedded in the surface along this groove 9. The rear end of the above perfusion passage pipe 10 is connected to a perfusion connection port 11 within a housing portion 7. Here a fine convex 13 is made on the surface at the inside of the arm 2, as shown in FIG. 2. And by caulking the convex, the perfusion passage pipe is fastened to the arm 2. A perfusing device of physiologic saline is connected to the above at perfusion connection port 11 and is used in combination with a high-frequency generator thereby to conduct a perfusing operation to regulate the flow rate at the tip 8 of the tweezers. This makes it possible to confirm any bleeding site and also to protect peripheral tissues from the heat generation derived from the high-frequency electricity.

Thanks to the above construction, one can prevent the tip portion 8 from becoming difficult to see when conducting the nipping operation of tweezers by embedding the perfusion passage pipe 10 in the inner surface of the arm 2, in consequence of which it gets possible to grasp the hemostatic or incising position exactly.

If the tweezers 1 of the present invention are used in the microscopically neurosurgical operation, such arrangement as shown in FIG. 4 is foreseen. The visual field of an operator is acquired mainly by the space between arms of bipolar electric coagulating and incising tweezers. Accordingly, if the tweezers 1 are arranged within the visual field S on the straight line ranging from the center R of the operator's visual field to the operational site Q, the above housing portion 7 and bipolar electric wire 12 come to enter into the operational field no longer.

As explained above, according to the instantly claimed tweezers, there can be acquired the visual field of an operator equal to that in the case of tweezers having no perfusion passage pipe and moreover, it becomes possible to conduct a perfusing operation, in consequence of which it gets possible to confirm any bleeding site. This enables one to minimize any damage on peripheral tissues caused by the heat generation from the high-frequency current and concurrently, to prevent such degradation in the coagulating and incising abilities as is involved when burnt tissue portions adhere to the tip portion of the tweezers.

In addition, by fixing a base in a range of 90° to 170° angled from the tip portion to the central axis of the grip portion of the above arm one can remove obstacles such as the above housing portion, bipolar electric wire or the like from the center of the operator's visual field. This results in being able to acquire a good visual field.

What is claimed is:

1. Bipolar electric surgical tweezers comprising:

two electrically conductive arms mutually isolated electrically from one another, and said arms acting as an independent bipolar electrode, said arms defining an instrument longitudinal axis, each said arm having an electrical connector for connection to an electrical source;

a perfusion connection port contained on a first of said arms, said port having a port axis;

and each of said arms having: a distal end defining a tip, and a proximal end;

wherein said first arm contains the perfusion connection port on its proximal end, and said first arm further contains a groove extending from said connection port to its tip, and a perfusion pipe located in said groove and connected to said port; and wherein said port axis and said longitudinal axis form an angle between 90° and 170°.

* * * * *